(12) United States Patent
Wang et al.

(10) Patent No.: US 8,192,947 B2
(45) Date of Patent: Jun. 5, 2012

(54) DETECTION OF SPECIFIC BINDING REACTIONS USING MAGNETIC LABELS

(75) Inventors: Yingxiao Wang, Champaign, IL (US); Mingxing Ouyang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 439 days.

(21) Appl. No.: 12/443,992

(22) PCT Filed: Oct. 12, 2007

(86) PCT No.: PCT/US2007/081173
§ 371 (c)(1),
(2), (4) Date: Oct. 15, 2009

(87) PCT Pub. No.: WO2008/046029
PCT Pub. Date: Apr. 17, 2008

(65) Prior Publication Data
US 2010/0041087 A1    Feb. 18, 2010

Related U.S. Application Data

(60) Provisional application No. 60/829,191, filed on Oct. 12, 2006.

(51) Int. Cl.
*C12Q 1/37* (2006.01)
(52) U.S. Cl. .......... 435/23; 436/518; 436/528; 436/164; 436/172; 422/50; 422/68.1; 422/82.05; 422/82.08
(58) Field of Classification Search ............. 435/23, 435/7.1; 436/518, 528, 164, 172; 422/50, 422/68.1, 82.05, 82.08
See application file for complete search history.

(56) References Cited

U.S. PATENT DOCUMENTS

| | | | |
|---|---|---|---|
| 2005/0196768 A1 | 9/2005 | Campbell et al. | 435/6 |
| 2006/0105953 A1* | 5/2006 | Lacoste et al. | 514/12 |
| 2006/0160111 A1 | 7/2006 | Piston et al. | 435/6 |

OTHER PUBLICATIONS

Shaner, Engineering Novel Fluorescent Proteins, 2006, pp. 107-136.*
Shaner et al., A guide to choosing fluorescent proteins, Nature Methods, Dec. 2005, vol. 2, No. 12, pp. 905-909.*
NCBI Accession No. AF506027 [gi:21464837] with Revision History—Jun. 19, 2002.
NCBI Accession No. AY678264 [9i:55420612] with Revision History—Nov. 21, 2004-Dec. 17, 2004.
NCBI Accession No. AY2678265 [gi:55420614] with Revision Hisotry—Nov. 21, 2004-Dec. 17, 2004.
Shaner et al., "Improved monomeric red, orange and yellow fluorescent proteins derived from *Discosoma sp.* Red fluorescent protein", Nature Biotechnology 2004 22(12):1567-1572.

* cited by examiner

*Primary Examiner* — Melanie J Yu
(74) *Attorney, Agent, or Firm* — Licata & Tyrrell P.C.

(57) ABSTRACT

The present invention is a novel biosensor composed of mOrange2 and mCherry fluorescent proteins operably linked via a linker, which provides a distinct color change upon separation of the fluorescent proteins.

6 Claims, 3 Drawing Sheets

SEQUENCE LISTING

<160> NUMBER OF SEQ ID NOS: 3

<210> SEQ ID NO 1
<211> LENGTH: 236
<212> TYPE: PRT
<213> ORGANISM: Artificial sequence
<220> FEATURE:
<223> OTHER INFORMATION: Synthetic fluorescent protein

<400> SEQUENCE: 1

```
Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 2
<211> LENGTH: 236
<212> TYPE: PRT
<213> ORGANISM: Artificial sequence
<220> FEATURE:
<223> OTHER INFORMATION: Synthetic fluorescent protein

<400> SEQUENCE: 2

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60
```

```
Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Cys Pro Lys Glu Ser Cys Asn Leu Phe Val Leu Lys Asp
1               5                   10
```

US 8,192,947 B2

DETECTION OF SPECIFIC BINDING REACTIONS USING MAGNETIC LABELS

INTRODUCTION

This patent application is a National Stage Application of International Application No. PCT/2007/081173 filed Oct. 12, 2007, which claims benefit of priority from U.S. Provisional Application Ser. No. 60/829,191 filed Oct. 12, 2006, teachings of which are herein incorporated by reference in their entirety.

BACKGROUND OF THE INVENTION

Traditional biochemical assays to detect intracellular activities, including immunoblotting and immunostaining, require the cell lysis or fixation, which can result in the alteration or loss of biologically relevant information. The application of fluorescence resonance energy transfer (FRET) can detect the intracellular signals in live cells with high spatiotemporal resolution, and hence provide more accurate and detailed information. FRET occurs when two fluorophores are in proximity, with the emission spectrum of the donor overlapping the excitation spectrum of the acceptor. Conventional FRET is based upon the cyan and yellow fluorescent protein pair (CFP and YFP, respectively). However, this biosensor only allows a single molecular activity to be visualized in live cells.

A variety of new fluorescence proteins with different colors have been developed (Shaner, et al. (2004) *Nature Biotechnology* 22:1567-1572). However, specific FRET pairs amongst these new fluorescent proteins are limited.

To simultaneously visualize more than one molecular event in the same cell, two spectrally distinctive pairs of fluorescence proteins capable of FRET are needed in the art. The present invention meets this need in the art.

SUMMARY OF THE INVENTION

The present invention is a biosensor composed of mOrange2 and mCherry fluorescent proteins operably linked via a linker, wherein said proteins participate in fluorescence resonance energy transfer (FRET). In particular embodiments, the linker contains a protease recognition sequence. A method for detecting the activity of a protease using the biosensor of this invention is provided, as is a system for detecting the activity of two distinct molecular events in a cell, wherein the system is composed of the mOrange2 and mCherry biosensor and a cyan and yellow fluorescence protein FRET pair. Kits containing a mOrange2/mCherry biosensor are also embraced by the present invention.

DETAILED DESCRIPTION OF THE INVENTION

Figure 1:
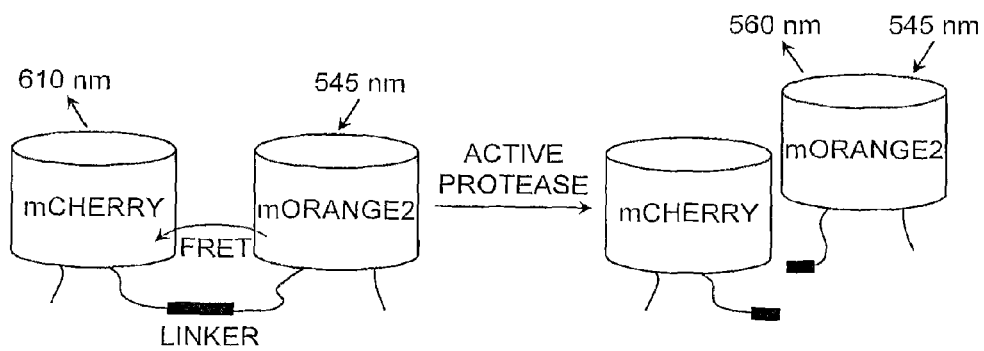
FIG. 1 is a schematic drawing showing the activation mechanism of a biosensor composed of mOrange2 and mCherry fluorescent proteins operably linked via a cleavable linker.

A novel biosensor for detecting a molecular event, such a protease activity, protein complex formation, or protein folding, has been produced. The biosensor is composed of a modified version of mOrange (mOrange2), and mCherry (see Shaner, et al. (2004) *Nature Biotechnology* 22:1567-1572). It has now been shown that these two fluorescent proteins, when operably linked or connected by a suitable linker, exhibit FRET. Moreover, when employing a linker with a protease recognition sequence, the two proteins can be separated upon protease cleavage so that FRET is abolished. The results presented herein indicate that mOrange2 and mCherry can be used alone or together with, e.g., CFP and YFP in assays for monitoring one or more cell signaling events in the same live cell using FRET technology.

mOrange and mCherry are described in the art (see, e.g., Shaner, et al. (2004) supra and U.S. Patent Application No. 20050196768). mOrange, with excitation and emission maxima of 548 nm and 562 nm, respectively, is an engineered variant of monomeric red fluorescent protein mRFP1 known in the art under GENBANK Accession No. AY678265 and set forth herein as SEQ ID NO:1. mOrange2 was generated by introducing four mutations (Gln64His, Phe99Tyr, Glu160Lys, and Gly196Asp) into mOrange (SEQ ID NO:1), thereby producing a protein with several fold higher photostability than mOrange. mCherry, with excitation and emission maxima of 587 nm and 610 nm, respectively, is also an engineered variant of monomeric red fluorescent protein mRFP1, which is known in the art under GENBANK Accession No. AY678264 and set forth herein as SEQ ID NO:2. In addition to certain point mutations, both mOrange and mCherry include the mRFP1 amino acid sequence set forth in GENBANK Accession Number AF506027, wherein N- and C-termini are replaced with equivalent residues from EGFP.

The linker, which operably links mCherry and mOrange2, can be any molecule which creates the appropriate distance between mCherry and mOrange2 so that the mOrange2 and mCherry participate in FRET. Because FRET is a distance-dependent interaction, an appropriate distance for the donor and acceptor FRET pair is typically in the range of 10-60 Å. Thus, in some embodiments, the linker is a 4-50 amino acid residue peptide. In other embodiments, the linker is a 7-20 amino acid residue peptide. In still other embodiments, the linker contains a protease recognition sequence, which is capable of being cleaved by a protease (e.g., a serine protease, cysteine protease, etc.), thereby disrupting FRET between mCherry and mOrange2. Such protease recognition sequences are well-known in the art and a comprehensive list of proteases and their cognate recognition sequences is available from the MEROPS database located on the world-wide web (see Rawlings, et al. (2002) *Nucl. Acids Res.* 30:343-346). Alternatively, the linker can be a protease-resistant peptide or a non-peptide linker (e.g., a carbohydrate). In certain embodiments, the linker is a protein, which upon proper folding, brings mCherry and mOrange2 into close proximity thereby producing FRET. Thus, in addition to loss of FRET, the present invention also provides for the appearance of FRET.

In the context of the present invention, the term "operably linked" refers to a functional linkage between two sequences. Generally, operably linked means that the two sequences being linked are contiguous and, in the context of protein coding regions, the resulting proteins are in the same reading frame.

The presently described mOrange2/mCherry biosensor can be used in a variety of in vivo and in vitro assays to detect, e.g., protease activity, protein complex formation, or protein folding. The amino acid sequences of the fluorescent proteins disclosed herein (e.g., mOrange, mCherry, CFP and YFP) are known, and the genes have been cloned, therefore, the biosensors of the invention can be made using recombinant methods, produced in vitro (e.g., using conventional cell-free techniques or chemical synthesis methods), or produced using a combination of in vitro and in vivo techniques.

Construction of expression vectors and recombinant production from the appropriate DNA molecules are performed by methods known in the art per se. Expression can be in prokaryotic or eukaryotic systems. Prokaryotes most frequently are represented by various strains of *E. coli*. However, other microbial strains can also be used, such as bacilli, for example *Bacillus subtilis*, various species of *Pseudomonas*, or other bacterial strains. In such prokaryotic systems, plasmid vectors which contain replication sites and control sequences derived from a species compatible with the host are used. For example, *E. coli* is typically transformed using derivatives of pBR322, a plasmid derived from an *E. coli* species discussed by Bolivar, et al. ((1977) *Gene* 2:95). Commonly used prokaryotic control sequences, which are defined herein to include promoters for transcription initiation, optionally with an operator, along with ribosome binding site sequences, including such commonly used promoters as the beta-lactamase (penicillinase) and lactose (lac) promoter systems (Change, et al. (1977) *Nature* 198:1056) and the tryptophan (trp) promoter system (Goeddel, et al. (1980) *Nucleic Acids Res.* 8:4057) and the lambda-derived $P_L$ promoter and N-gene ribosome binding site (Shimatake, et al. (1981) *Nature* 292:128). Any available promoter system compatible with prokaryotes can be used.

Expression systems useful in the eukaryotic hosts generally include promoters derived from appropriate eukaryotic genes. A class of promoters useful in yeast include, for example, promoters for synthesis of glycolytic enzymes, including those for 3-phosphoglycerate kinase (Hitzeman, et al. ((1980) *J. Diol. Chem.* 255:2073). Other promoters include those from the enolase gene (Holland, et al. (1981) *J. Biol. Chem.* 256:1385) or the Leu2 gene obtained from YEp13 (Broach, et al. (1978) *Gene* 8:121).

Suitable mammalian promoters include the early and late promoters from SV40 (Fiers, et al. (1978) *Nature* 273:113) or other viral promoters such as those derived from polyoma, adenovirus II, bovine papilloma virus or avian sarcoma viruses.

The expression system is constructed from the foregoing control elements operably linked to nucleic acids encoding the biosensor disclosed herein using standard methods, employing standard ligation and restriction techniques which are well-understood in the art. Isolated plasmids, DNA sequences, or synthesized oligonucleotides are cleaved, tailored, and relegated in the form desired.

Correct ligation during plasmid construction can be confirmed by first transforming a suitable *E. coli* strain with the ligation mixture. Successful transformants are selected using a conventional selectable marker, e.g., ampicillin, tetracycline or other antibiotic resistance or using other markers depending on the mode of plasmid construction, as is understood in the art. Plasmid from the transformants can then be prepared according to conventional methods. See, e.g., the method of Clewell, et al. (1969) *Proc. Natl. Acad. Sci. USA* 62:1159. The isolated DNA is analyzed by restriction and/or sequenced according to standard laboratory practices.

The constructed vector is then transformed into a suitable host for production of the fluorescent protein or biosensor of interest. Depending on the host cell used, transformation is done using standard techniques appropriate to such cells. Calcium treatment employing calcium chloride, as described by Cohen ((1972) *Proc. Natl. Acad. Sci. USA* 69:2110), or the RbCl method described in Maniatis, et al. ((1982) *Molecular Cloning: A Laboratory Manual*, Cold Spring Harbor Press, p. 254) can be used for prokaryotes or other cells which contain substantial cell wall barriers. For mammalian cells without such cell walls, the calcium phosphate precipitation method of Graham and van der Eb, ((1978) *Virology* 52:546) or electroporation is preferred. Transformations into yeast can be carried out according to the method of Van Solingen, et al. ((1978) *J. Bacter.* 130:946) or Hsiao, et al. ((1979) *Proc. Natl. Acad. Sci. USA* 76:3829.

The transformed cells are then cultured under conditions favoring expression of the biosensor and the recombinantly produced protein recovered from the cells or cell supernatant. To facilitate purification, one or more tags can be incorporated into the biosensors of the invention. Exemplary tags include, e.g., His6, FLAG, and the like.

Combining the instant mCherry/mOrange2 biosensor with conventional biosensors such as CFP and YFP-based biosensors allows for the simultaneous visualization of two active cell signaling events in the same live cell. Such CFP/YFP biosensors can be composed of individual proteins or, like the instant biosensor can be fused together via a linker, which is responsive to a biochemical signal. Thus, in addition to the linkers already discussed, it is contemplated that the biosensors disclosed herein can contain linkers including, but not limited to, calmodulin protein as a calcium binding moiety (Palmer & Tsien (2006) *Nat. Protoc.* 1(3):1057-65), as well as indicators of phosphorylation events mediated by protein kinases such as PKB (Kunkel, et al. (2005) *J. Biol. Chem.* 280: 5581-5587), PKA (Zhang, et al. (2001) *Proc. Natl. Acad. Sci. USA* 98:14997-15002), PKC (Violin, et al. (2003) *J. Cell. Biol.* 161:899-909), and cdc42 (Itoh, et al. (2002) *Mol. Cell. Biol.* 22: 6582-6591; Seth, et al. (2003) *Biochemistry* 42:3997-4008).

The combination of multiple biosensors finds application in detecting different biomarkers with different colors in the same live cells thereby providing a more accurate diagnostic means to detect diseases, e.g., cancer, and providing double criteria to differentiate cancer versus normal cells and hence enhancing the fidelity of such assays. Detection of the different colors of the biosensors can be via any conventional method including, e.g., wide-field fluorescence microscopy or laser scanning confocal microscopy.

EXAMPLE 1 mOrange2/mCherry Protease Biosensor in vitro

By way of illustration, membrane-type 1-metalloproteinase (MT1-MMP) activity was monitored using the mOrange2 and mCherry FRET pair. MT1-MMP is a membrane-anchored enzyme belonging to matrix metalloproteinase (MMP) family. MT1-MMP is known to digest MMP-2, another member of MMP family, as well as extracellular matrix protein collagen. A specific and sensitive MT1-MMP biosensor based on mOrange2 and mCherry was generated utilizing mCherry at the N-terminus and mOrange2 at the C-terminus with a substrate sequence derived from MMP-2 (Cys-Pro-Lys-Glu-Ser-Cys-Asn-Leu-Phe-Val-Leu-Lys-Asp, SEQ ID NO:3, wherein the underlined amino acids Asn-Leu form the cutting site recognizable by MT1-MMP) located between mCherry and mOrange2.

The basis of this assay is that when MT1-MMP is inactive, the mCherry and mOrange2 are positioned in proximity and favor a strong FRET between the two moieties (FIG. 1). Therefore, the excitation of mOrange2 at 545 nm leads to the emission of mCherry at 610 nm. When MT1-MMP is activated, it cleaves the designed substrate sequence, which leads to the separation of the mCherry from the mOrange2 and the decrease in the FRET efficiency. The excitation of mOrange2 at 545 nm then results in the emission from mOrange2 at 560 nm and no emission from mCherry (FIG. 1) Hence, the emission ratio of mCherry/mOrange2 with the excitation of mOrange2 serves as a reliable and sensitive indicator of the status of MT1-MMP activation.

The use of the instant of mCherry/mOrange2 biosensor was subsequently demonstrated in vitro. A cDNA encoding the MT1-MMP was cloned into the PRSETb vector and transformed in bacterium BL21 (DE3). After the induction of the protein expression with IPTG, the bacteria were lysed and the MT1-MMP protein was purified with B-PER 6xHis Fusion Protein Purification Kit (Pierce, Rockland, Ill.). When compared with a purified CFP/YFP-based Src biosensor, the mCherry/mOrange2-based MT1-MMP biosensor provided a clearly distinct color.

Figure 2:
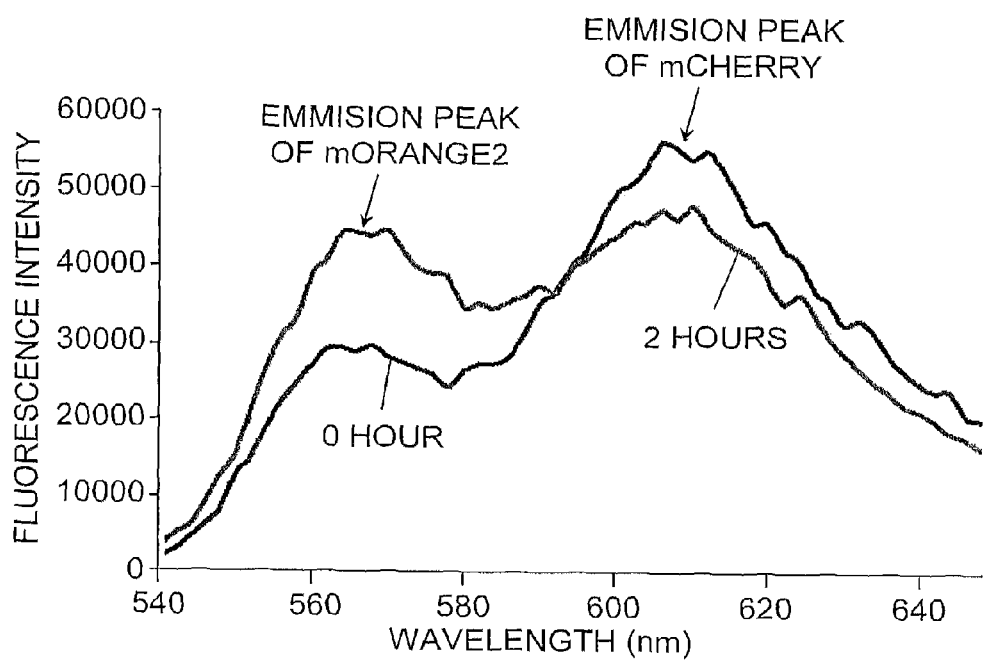
FIG. 2 shows emission spectra of the MT1-MMP biosensor before (0 hour) and after the addition of MT1-CAT for 2 hours.

To demonstrate that the MT1-MMP could cause a FRET change of the recombinant mCherry/mOrange2-based MT1-MMP biosensor, the mCherry/mOrange2-based MT1-MMP biosensor protein was incubated with the catalytic domain of MT1-MMP (MT1-CAT). The reaction was carried out in a buffer composed of 50 mM HEPES buffer, pH 6.8, 10 mM $CaCl_2$, 0.5 mM $MgCl_2$, 50 μM $ZnCl_2$, and 0.01% BRIJ-35 at 37° C. Excitation of the biosensor was achieved at 515 nm. The emission spectra (540-640 nm) of the biosensor were scanned with a TECAN SAFIRE II fluorescence plate reader before and after the application h of MT1-CAT (FIG. 2). The addition of MT1-CAT increased mOrange2 emission at the expense of mCherry emission, representing a typical loss of FRET. Hence, MT1-CAT caused a FRET decrease of the mCherry/mOrange2-based MT1-MMP biosensor.

It was further examined whether the FRET change of mCherry/mOrange2-based MT1-MMP biosensor caused by MT1-CAT was due to the cleavage of the biosensor. The mCherry/mOrange2-based MT1-MMP biosensor was incubated with MT1-CAT for in vitro cleavage assay. The assay mixture was subsequently subjected to SDS-PAGE and staining with COOMASSIE blue. Without the addition of MT1-CAT, the mCherry/mOrange2-based MT1-MMP biosensor was intact with molecular weight about 60-70 KD. In the presence of MT1-CAT (2 hour incubation), the mCherry/mOrange2-based MT1-MMP biosensor was cleaved into two pieces of about 30 KD. The results of this analysis indicated that MT1-CAT cleaved the mCherry/mOrange2-based MT1-MMP biosensor.

EXAMPLE 2 mOrange2/mCherry Protease Biosensor in vivo

Figure 3:
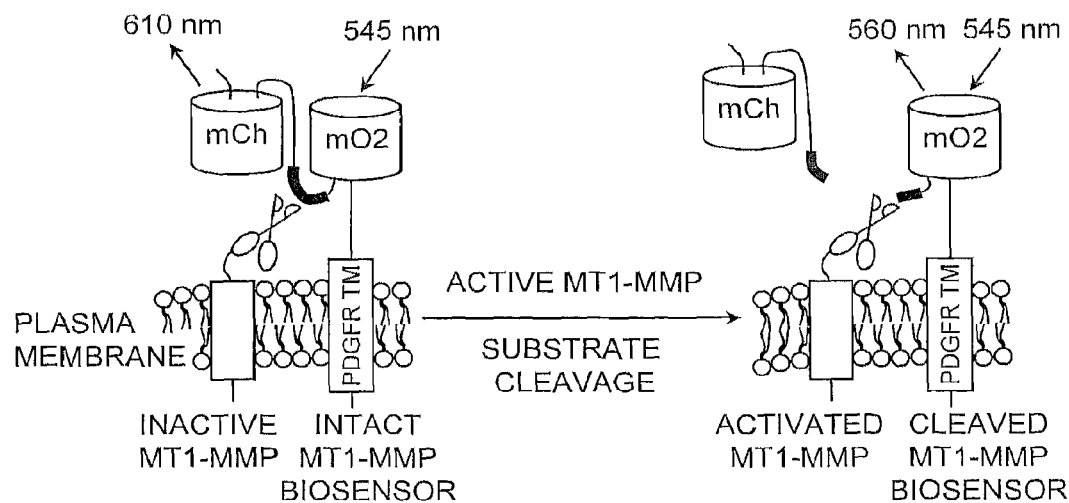
FIG. 3 is a schematic drawing showing a membrane-tethered MT1-MMP biosensor. The sensing element of the MT1-MMP biosensor is anchored on the extracellular surface of plasma membrane. Activation of MT1-MMP results in cleavage of the protease recognition sequence linker located between mOrange2 (mO2) and mCherry (mCh), thereby causing FRET to decrease.

The catalytic domain of MT1-MMP and the transmembrane domain of the platelet-derived growth factor receptor beta (i.e., PDGFRβ) are known to co-localize at the cell surface. Accordingly, a cDNA encoding the MT1-MMP biosensor described herein (see Example 1) was fused with a nucleic acid molecule encoding the transmembrane domain of PDGFRβ, resulting in the fusion construct designated "PDGFR™". This construct was designed so that the linker of the biosensor was located in the extracellular space, but in close proximity to the MT1-MMP catalytic domain (FIG. 3).

Figure 4:
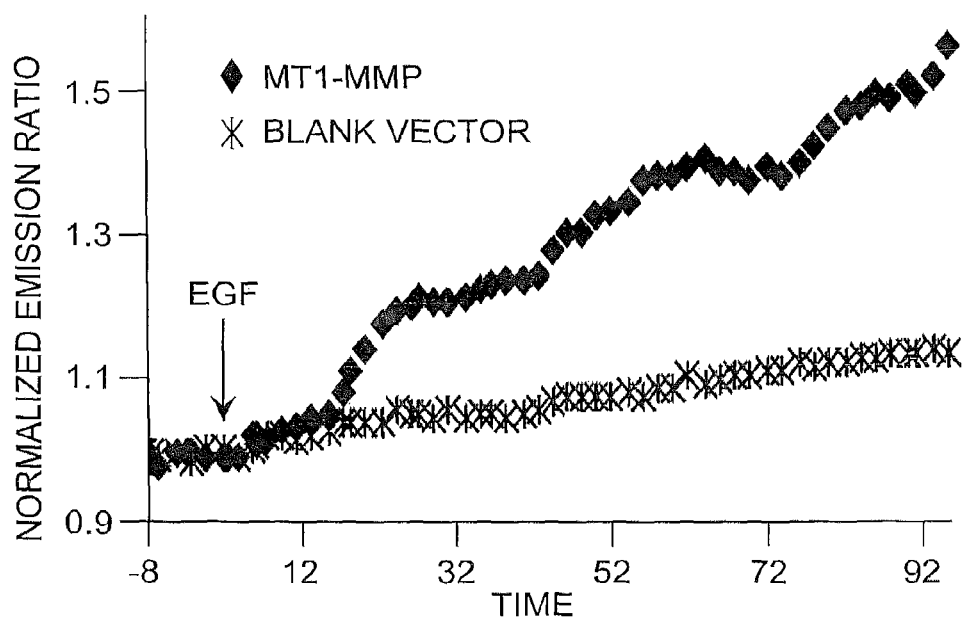
FIG. 4 shows that the MT1-MMP biosensor is sensitive to MT1-MMP in HeLa cells. HeLa cells were transfected with constructs encoding a MT1-MMP biosensor and MT1-MMP or blank vector. The transfected cells were subjected to 50 ng/ml EGF stimulation for various periods of time. FRET ratio images of transfected cells, before and after EGF stimulation, were analyzed. Normalized time courses of averaged FRET ratios before and after EGF stimulation is shown.

Nucleic acid molecules encoding the mOrange2/mCherry MT1-MMP biosensor construct and MT1-MMP were introduced into mammalian HeLa cells. Epidermal growth factor (EGF) is known in the art to induce MT1-MMP, therefore EGF was added to the recombinant HeLa cells. The results indicate that EGF induced a significant FRET change of the MT1-MMP biosensor in HeLa cells co-transfected with MT1-MMP, but not blank control vector. Normalized time courses of FRET ratios (FIG. 4) confirmed the results obtained by FRET ratio image analysis. Therefore, the mOrange2/mCherry MT1-MMP biosensor was sensitive to MT1-MMP activity in live mammalian cells.

EXAMPLE 3 mOrange2/mCherry and CFP/YFP-Based Biosensors

Figure 5:
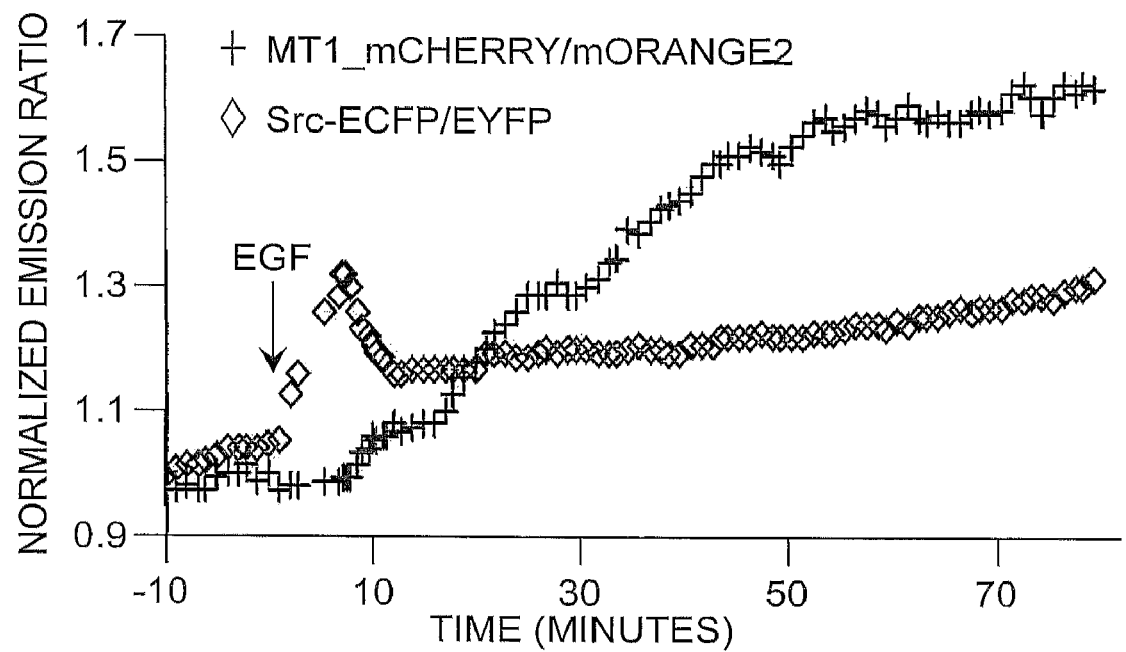
FIG. 5 shows that the mOrange2/mCherry-based MT1-MMP biosensor can be combined with a CFP/YFP-based Src biosensor to visualize both MT1-MMP and Src activities simultaneously in the same live mammalian cells. HeLa cells were transfected with MT1-MMP biosensor and Src biosensor together with MT1-MMP. The transfected cells were subjected to 50 ng/ml EGF stimulation for various periods of time. FRET ratio images of the biosensor were analyzed. Normalized time courses of averaged FRET ratios of the MT1-MMP biosensor (MT1_mCherry/mOrange2) and Src biosensor (Src_ECFP/EYFP) before and after EGF stimulation are shown.

To demonstrate the utility of the instant biosensor in monitoring multiple molecule events in vivo, the mOrange2/mCherry-based MT1-MMP biosensor was combined with a CFP/YFP-based Src biosensor to simultaneously visualize MT1-MMP and Src activity in the same live mammalian cells. The results indicated that EGF induced a fast and global activation of Src, while the MT1-MMP activation upon EGF stimulation was relatively slow and concentrated at the cell periphery. Normalized time courses of averaged FRET ratios also indicated that the activation of Src was fast with a transient peak at around 5 minutes of EGF stimulation, while the MT1-MMP activation was delayed with sustained increase (FIG. 5). These results indicated that the mOrange2/mCherry biosensor could be combined with CFP/YFP-based biosensor to visualize two active signaling events simultaneously in the same live cells.

What is claimed is:

1. A biosensor comprising mOrange2 and mCherry fluorescent proteins operably linked via a linker, wherein said proteins participate in fluorescence resonance energy transfer (FRET).

2. The biosensor of claim 1, wherein the linker contains a protease recognition sequence.

3. A method for detecting the activity of a protease comprising contacting the biosensor of claim 2 with a protease and detecting a change in the FRET of the fluorescent proteins, wherein a change in the FRET is indicative of cleavage of the linker by the protease.

4. A system for detecting the activity of two distinct molecular events in a cell, the system comprising the biosensor of claim 1 and a cyan and yellow fluorescence protein FRET pair.

5. A kit comprising the biosensor of claim 1.

6. The kit of claim 5, further comprising a cyan and yellow fluorescence protein FRET pair.

* * * * *